US009409171B2

(12) United States Patent

Kurowski et al.

(10) Patent No.: US 9,409,171 B2
(45) Date of Patent: Aug. 9, 2016

(54) MICROFLUIDIC STRUCTURE HAVING RECESSES

(71) Applicant: Boehringer Ingelheim MicroParts GmbH, Dortmund (DE)

(72) Inventors: Dirk Kurowski, Gevelsberg (DE); Oliver Paul, Gelsenkirchen (DE)

(73) Assignee: Boehringer Ingelheim MicroParts GmbH, Dortmund (DE)

( * ) Notice: Subject to any disclaimer, the term of this patent is extended or adjusted under 35 U.S.C. 154(b) by 0 days.

(21) Appl. No.: 14/719,503

(22) Filed: May 22, 2015

(65) Prior Publication Data

US 2015/0251182 A1 Sep. 10, 2015

Related U.S. Application Data

(63) Continuation of application No. 14/127,341, filed as application No. PCT/EP2012/062863 on Jul. 2, 2012, now abandoned.

(30) Foreign Application Priority Data

Jul. 5, 2011 (EP) .................................... 11172775

(51) Int. Cl.
*B01L 3/00* (2006.01)
*B01D 35/00* (2006.01)
*G01N 33/50* (2006.01)

(52) U.S. Cl.
CPC ......... *B01L 3/502746* (2013.01); *B01L 3/5027* (2013.01); *B01L 3/502738* (2013.01); (Continued)

(58) Field of Classification Search
CPC ................ B01L 2200/0684; B01L 2200/0621; B01L 2400/0406; B01L 2400/086; B01L 2400/084; B01L 3/5027; B01L 3/502738; B01L 3/502746; B01L 3/502723; B01L 2300/0864
See application file for complete search history.

(56) References Cited

U.S. PATENT DOCUMENTS 4,271,119 A 6/1981 Columbus
4,618,476 A 10/1986 Columbus
(Continued)

FOREIGN PATENT DOCUMENTS

EP 0153110 A2 8/1985
EP 1616619 A1 1/2006
(Continued)

OTHER PUBLICATIONS

Abstract in English for EP1616619, 2006.
(Continued)

*Primary Examiner* — Jennifer Wecker
(74) *Attorney, Agent, or Firm* — Michael P. Morris; Alan R. Stempel

(57) ABSTRACT

The invention relates to a microfluidic structure (1), comprising at least one cavity (10) having at least one inlet opening (11) and at least one outlet opening (12), wherein the cavity (10) can be filled with a liquid or a liquid can flow through the cavity and at least one element (13) is provided inside the cavity (10), which element stops the flow of the liquid at least temporarily and/or diverts the flow of the liquid at least in some regions within the cavity (10).
According to the invention, the at least one element (13) is formed by a recess (13) introduced into a wall of the cavity (10), which recess (13) has at least one first region (14) at which the liquid stops at least temporarily and/or is diverted at least in some regions and at least one second region (15) at which the liquid preferably flows into the recess (13).
Such a microfluidic structure makes it possible to fill the cavity (10) without air inclusions. Thereby, the useful volume of the cavity (10) is not limited, and the production costs of a microfluidic component (2) having such a microfluidic structure (1) can be kept low.

8 Claims, 6 Drawing Sheets

Figure 1:
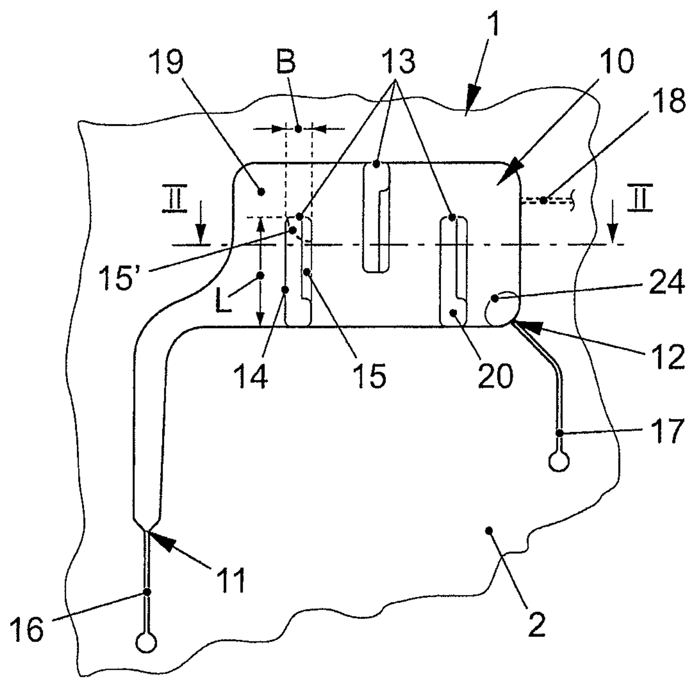

(52) U.S. Cl.
CPC ...... *B01L3/502723* (2013.01); *B01L 3/502753* (2013.01); *B01L 2200/0642* (2013.01); *B01L 2200/0684* (2013.01); *B01L 2300/0809* (2013.01); *B01L 2300/0858* (2013.01); *B01L 2300/0864* (2013.01); *B01L 2400/0406* (2013.01); *B01L 2400/084* (2013.01); *B01L 2400/086* (2013.01)

(56) References Cited

U.S. PATENT DOCUMENTS

2004/0232074 A1* 11/2004 Peters .................... B01D 61/18 210/634
2006/0216195 A1 9/2006 Blankenstein et al.
2006/0249387 A1* 11/2006 Willms ............. B01L 3/502715 204/451
2007/0125434 A1* 6/2007 Nakao ............... B01L 3/502723 137/806
2007/0269893 A1* 11/2007 Blankenstein .... B01L 3/502723 436/2

FOREIGN PATENT DOCUMENTS

EP 1685900 A1 8/2006
EP 1792655 A1 6/2007

OTHER PUBLICATIONS

International Search Report, Form PCT/ISA/210, and Written Opinion, Form PCT/ISA/237, for corresponding application PCT/EP2012/062863, date of mailing Oct. 17, 2012.

* cited by examiner

MICROFLUIDIC STRUCTURE HAVING RECESSES

The invention relates to a microfluidic structure comprising at least one cavity with at least one inlet opening and at least one outlet opening, the cavity being adapted to be filled with a liquid or have a liquid flow through it, and at least one element being provided within the cavity which at least temporarily stops and/or at least partly diverts the liquid as it flows within the cavity.

Microfluidic structures are components of microfluidic platforms or microfluidic components and essentially comprise cavities and/or channels in which sample liquids that are to be investigated or manipulated can be held and transported by suitable means (e.g. by capillary forces, pressure differences created) to reaction sites provided accordingly.

In particular, the present invention encompasses microfluidic platforms such as for example sample carriers, test strips, biosensors or the like which may be used for carrying out individual tests or measurements. For example, biological liquids (e.g. blood, urine or saliva) may be investigated, on the one hand, for pathogens and incompatibilities but also, on the other hand, for their content of for example glucose (blood sugar) or cholesterol (blood fat). For this purpose corresponding detection reactions or entire reaction cascades take place on the microfluidic platforms.

For this it is necessary for the biological sample liquid to be transported by suitable means to the reaction site or sites provided for this purpose. This transporting of the sample liquid may be carried out for example by passive capillary forces (using corresponding capillary systems or microchannels) or by means of active actuating elements. Injection or membrane pumps, for example, may be used as the active actuating elements and may be located outside the microfluidic platform or on the platform and produce a corresponding pressure within a microfluidic structure consisting in particular of microchannels and microcavities.

In general, microfluidic platforms comprise a sample input region of the order of a few millimeters in size for introducing a quantity of sample liquid of the order of a few microliters, while the sample liquid (such as blood) has to be transported through a microchannel or through a microchannel system to corresponding cavities containing for example chemical reagents in dried form.

In order that a sample liquid can undergo a satisfactory detection reaction with the reagents in a cavity, it is essential that the cavity is filled as completely and uniformly as possible.

When filling large cavities, particularly those that are broad and irregularly shaped, for example with lengths and/or width dimensions of several millimeters and a resulting volume range from for example 10 μl to about 10 ml, there is the problem that the cavity does not fill uniformly and thus air inclusions or air bubbles may form in the cavity. As a result, the whole of the volume of the cavity is not available for the sample liquid. Dry substances stored in such a cavity, for example, are thus not sufficiently dissolved and the formation of clumps may occur, thus adversely affecting a desired detection reaction.

According to the prior art, a remedy is offered by providing bar-like elements in the cavity arranged in such a way that the liquid in the cavity has to flow in a meandering direction.

However, a disadvantage of this structure is that the bar-like elements take up space within the cavity which is actually needed.

Therefore, to compensate, more space has to be provided on the microfluidic platform or microfluidic component. This should be avoided in particular for microfluidic platforms, on account of the associated increase in manufacturing costs.

A microfluidic structure or a microfluidic platform for filling without any air bubbles is known from DE 103 60 220 A1. Specifically, a cavity is provided having an inlet opening and an outlet opening. In the region of the inlet opening the cavity comprises microstructural elements in the form of pillars. This region forms an area of increased capillary force. The increased capillary force initially causes total wetting, free from air bubbles, of the entry region of the cavity with the sample liquid. The part of the cavity facing the outlet opening is only wetted subsequently.

In order to accelerate the transporting of liquid, a ramp is provided in the cavity which raises the level of the cavity base to the level of the outlet opening.

An arrangement of this kind is unsatisfactory for filling cavities that are large, particularly broad (at right angles to the direction of inflow or throughflow of the liquid) and irregularly shaped.

The invention is therefore based on the problem of improving a microfluidic structure according to the preamble of claim 1 so as to allow improved filling, particularly of large cavities, particularly substantially free from air bubbles.

The problem is solved with the charactering features of claim 1. Advantageous further features of the invention can be found in the subclaims.

The invention therefore starts from a microfluidic structure comprising at least one cavity having at least one inlet opening and at least one outlet opening, the cavity being adapted to be filled with a liquid or have such a liquid flow through it and within the cavity is provided at least one element which at least temporarily stops and/or at least partially deflects the liquid as it flows within the cavity.

According to the invention it is envisaged that the at least one element is formed by a recess provided in a wall of the cavity, which has at least one first region at which the liquid is at least temporarily stopped and/or at least partially deflected and at least one second region at which the liquid preferably flows into the recess.

On reaching the second region the liquid flows immediately, i.e. without any appreciable stop, into the recess and, beyond a specified fill level of the recess, also draws the liquid that has initially stopped in the first region of the recess into the recess with it.

In this way the liquid in the cavity can be controlled such that the cavity is filled uniformly and substantially free from air bubbles. This is possible even with cavities that are large, particularly wide and irregular in shape which have, for example, a fill volume of the order of about 10 μl to 10 ml.

It should be noted that the above-mentioned wall of the cavity may be, for example, a base of the cavity. However, any other walls of the cavity are also conceivable. Thus, in a suitable configuration of a lid closing of the cavity, the wall may also be formed by the latter, for example. A combination of these two possibilities is also possible, for example.

According to a further feature of the invention, it is envisaged that the second region is formed by a ramp-like transition which starts from a base level of the cavity and extends to a base level of the recess.

This ramp-like transition ensures, in a simple manner, that the sample liquid flows into the recess at this point, without stopping, and fills the recess.

It has proved advantageous if the ramp-like transition, starting from a boundary edge of the recess, forms an angle of about 10° to 60°, most preferably about 45°, with a base plane of the cavity. Tests have shown that the desired flow characteristics of the liquid can best be achieved by such a choice of geometric parameters.

However, instead of a ramp-like configuration, other configurations of the second region would also be possible. Thus the second region could also be formed by a "soft" transition, for example by a convex or concave rounded portion. A notch-like structure (looking at the recess in plan view) is also conceivable.

The first region, by contrast, is expediently formed by a boundary edge of the recess at which the convergent walls that form the boundary edge enclose an angle of less than 120°, preferably approximately between 95° and 70°, most preferably about 90°.

In this way the first region reliably forms a capillary stop at which the inflowing liquid is initially stopped or deflected.

It has also proved highly advantageous in tests if the at least one recess is of elongate configuration, the at least one first region facing an incoming liquid and the at least one second region being remote from an incoming liquid. Thus the incoming liquid can be controlled so that initially it reaches the first region, is stopped there, deflected and on reaching the second region preferably runs into the recess (without any appreciable stop) and fills it. With a corresponding arrangement of a plurality of recesses with one another, the desired control of the liquid can be adapted to the specific length of a cavity.

The recess may be approximately rectangular, for example, in plan view. However, it may also be of a different shape in plan view, for example arcuate. This may be expedient, for example, when the cavity that is to be filled is also of arcuate configuration in its longitudinal extent.

According to another expedient embodiment of the inventive concept, a plurality of recesses are provided which are arranged alternately, starting from the side walls of the cavity.

In this way it is possible to create a meandering flow path for the liquid with the recesses in the cavity that is to be filled.

It has also proved advantageous if the at least one first region extends substantially over the entire length of a longitudinal side of the at least one recess and the at least one second region extends over only part of the length of another longitudinal side.

In this way it is possible on the one hand to ensure a capillary stop over a wide front while on the other hand ensuring a time-delayed inflow of liquid into the recess, while additional volume can be obtained at the point where the second region is not formed.

However, the invention also relates to a microfluidic platform having at least one microfluidic structure according to at least one of claims 1 to 7. A microfluidic platform thus configured can be manufactured cheaply and meets high demands for a reliable, particularly bubble-free filling of the cavities present.

Figure 2:
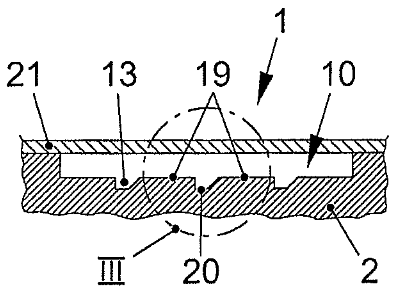
Figure 3:
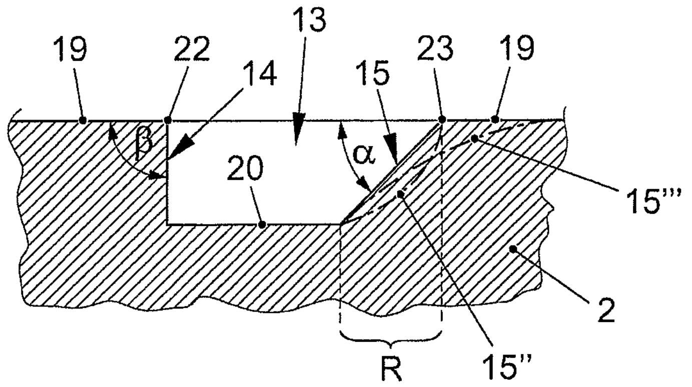
Figure 4A:
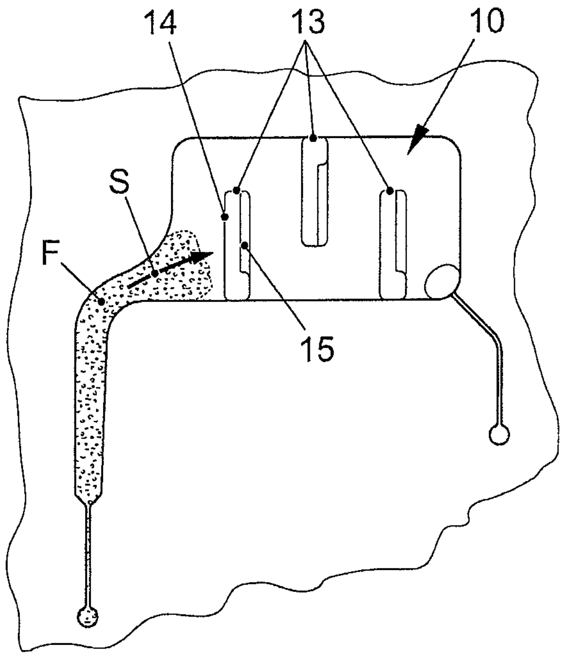
Figure 4B:
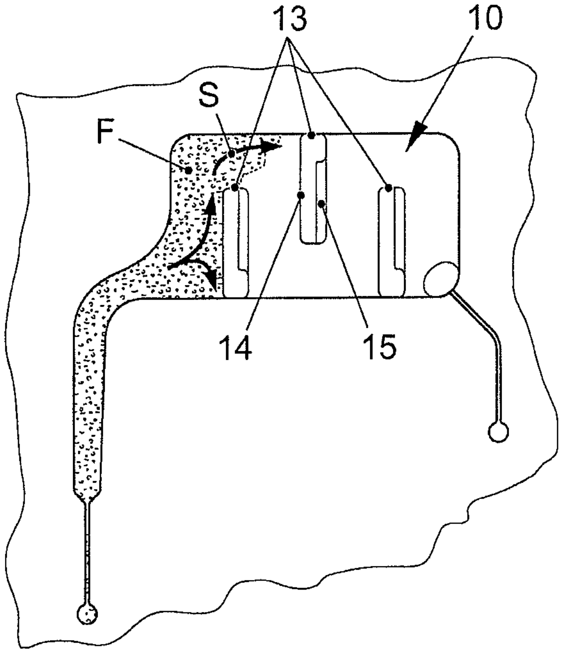
Figure 4C:
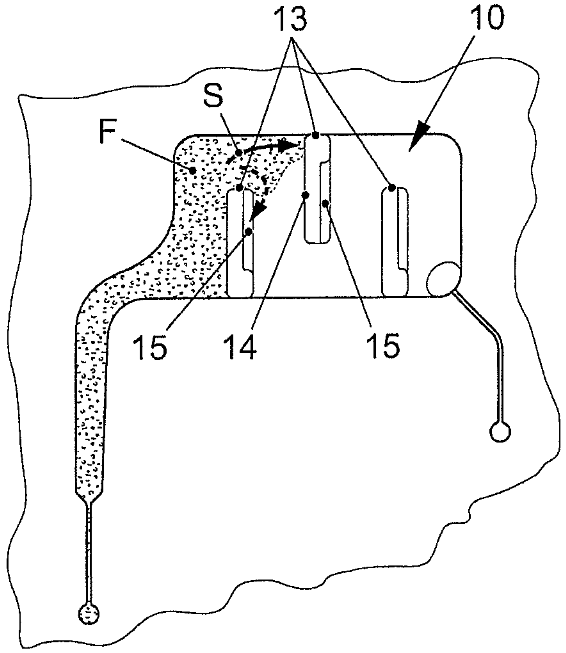
Figure 4D:
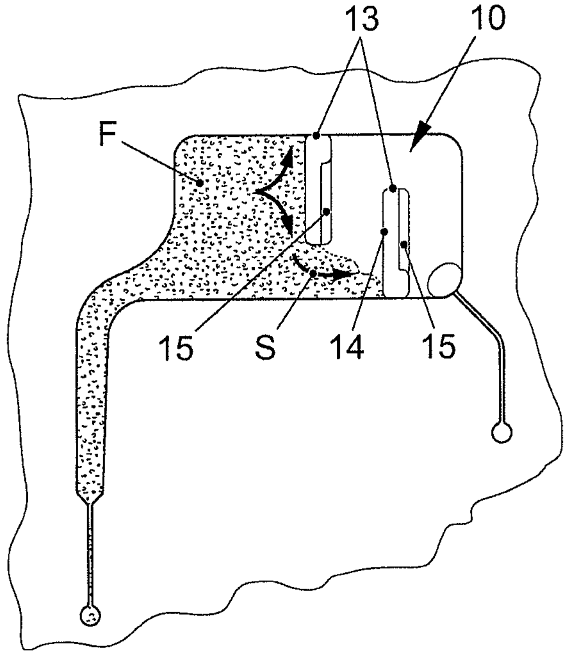
Figure 4E:
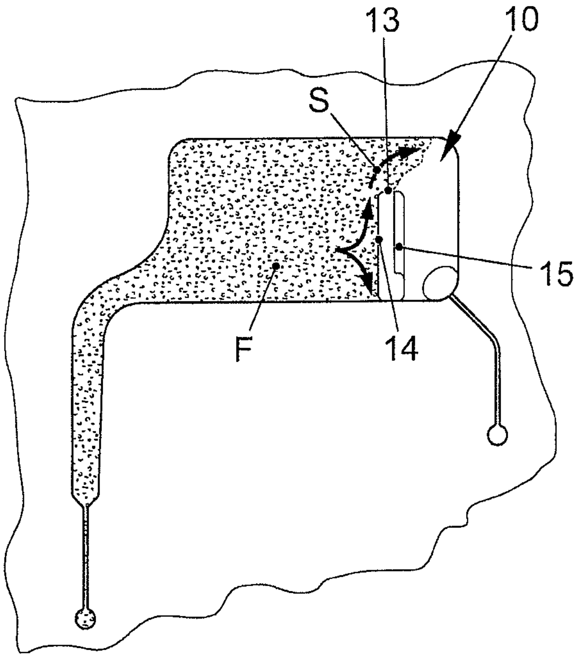
Figure 4F:
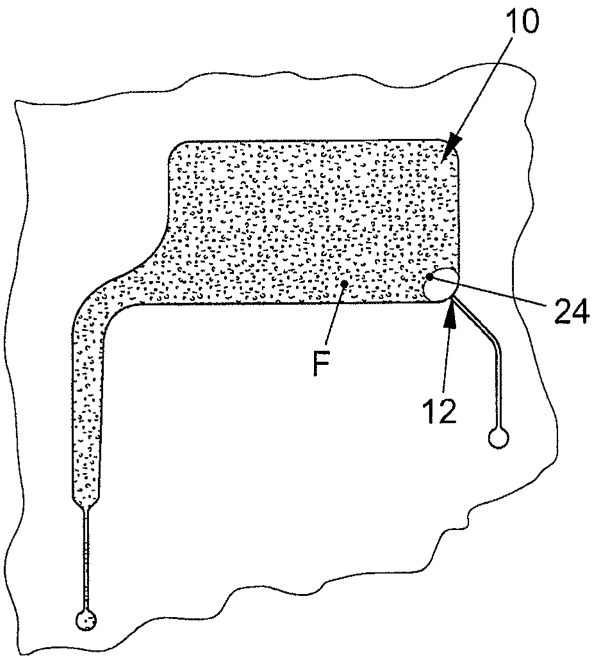
Figure 5:
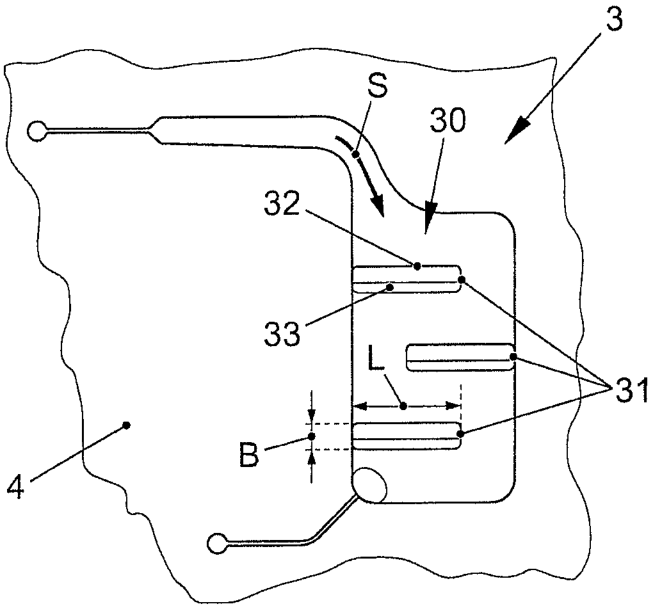
Figure 6:
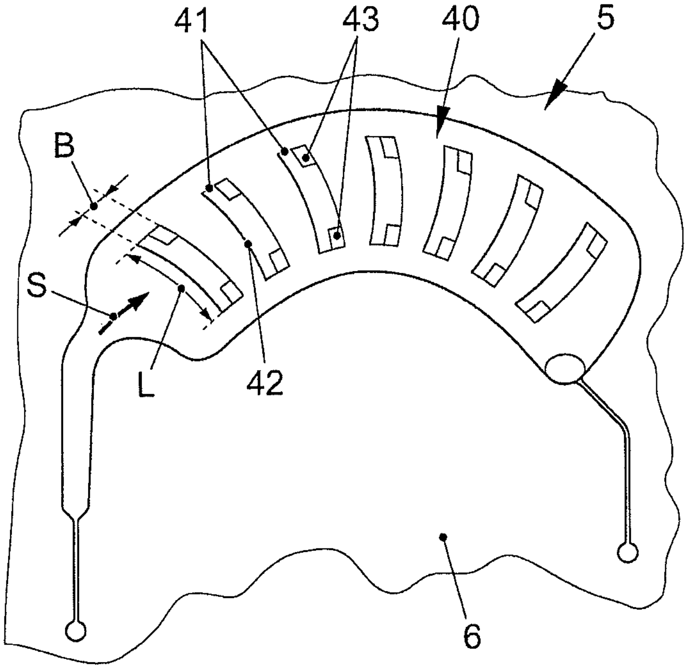
Figure 7:
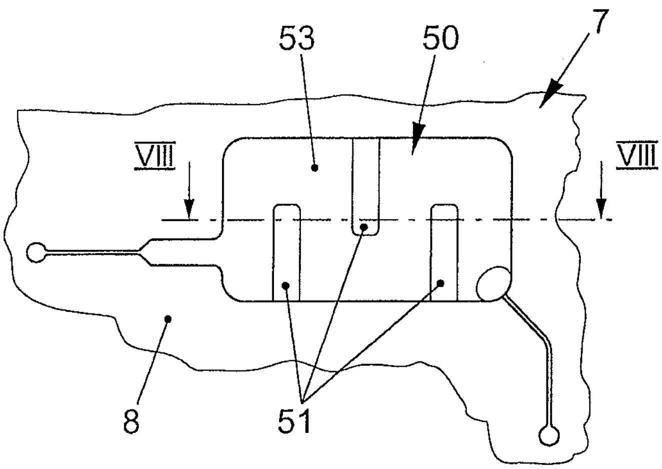
FIG. 7 (Prior Art)
Figure 8:
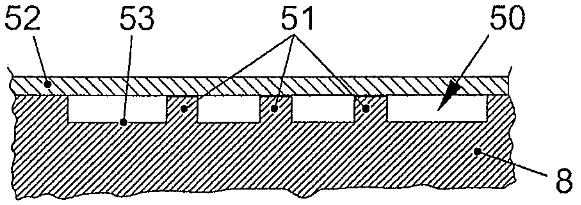

Further advantages and embodiments of the invention will become clear from embodiments by way of example, as will be explained with the aid of the accompanying drawings, wherein:

FIG. 1 shows a microfluidic structure according to a first preferred embodiment in plan view, in schematic form, FIG. 2 is a sectional view of the microfluidic structure along section line II in FIG. 1, FIG. 3 is a detailed view III from FIG. 2, FIGS. 4*a* to 4*f* show different stages of filling the microfluidic structure according to FIG. 1 with a liquid, FIG. 5 shows a microfluidic structure in plan view according to a second embodiment, in schematic form, FIG. 6 shows a microfluidic structure in plan view according to a third embodiment, in schematic form, FIG. 7 shows a microfluidic structure according to the prior art and FIG. 8 shows a sectional view along section line VIII in FIG. 7.

First of all, reference will be made to FIGS. 1 to 3.

These figures show a microfluidic structure 1 introduced into a microfluidic component 2. The microfluidic structure 1 comprises a cavity 10 which has a fill volume of about 15 μl. The cavity 10 is irregularly shaped and is provided with an inlet opening 11 which connects the cavity 10 to a fill channel 16. The fill channel 16 itself may be connected to a fill opening (for example a sample input region) which is not specifically designated.

On the other side the cavity 10 is provided with an outlet opening 12 which for example opens up the fluidic connection to a venting channel 17. In the region of the outlet opening 12 a capillary stop 24 is also provided in conventional manner.

Additionally or alternatively the cavity 10 may be connected through an outlet opening with another microchannel 18 (shown by dashed lines) if a liquid is to be transported through the cavity 10 into another cavity, for example (not shown).

The cavity 10 is a comparatively large cavity measuring about 12 mm wide, 36 mm long and about 1.5 mm deep.

It should also be noted that there are three recesses 13 within the cavity 10. Each recess 13 is substantially rectangular in appearance, in plan view, with a length L and a width B. The recesses 13 are arranged alternately, starting from longitudinal sides of the cavity 10.

It can be seen that each recess 13 comprises a first region 14 which faces an incoming liquid F (see FIG. 4) and at which the incoming liquid F is at least temporarily stopped and/or at least partly deflected.

Moreover, each recess 13 is provided with a second region 15 at which an incoming liquid F flows into the recess 13 without being stopped.

The cavity 10 is closed off by a cover 21 (for example a film attached by adhesion) and comprises a base 19. Each recess 13 comprises a base 20.

The detailed view in FIG. 3, in particular, shows that the first region 14 (capillary) is formed by a boundary edge 22 of the recess 13 at which the convergent walls forming the boundary edge 22 make an angle β which is 90°. In a departure from the embodiment shown, other angles are naturally possible and may be greater than or less than 90°.

It can also be seen that the second region 15 is formed by a ramp-like transition R which, starting from the base level 19 of the cavity 10, extends to a base level 20 of the recess 13.

In particular it can be seen that the ramp-like transition R, starting from a boundary edge 23 of the recess 13, forms an α of about 45 degrees with the base plane 19 of the cavity 10. Here, too, angles greater than or less than 45° are possible.

It should be noted that the second region 15 does not necessarily have to be formed by a ramp-like transition but that other embodiments are also possible. Thus, FIG. 3 shows that the second region may for example also be formed by a "soft" transition, for example a concave 15" or convex 15"' rounded portion.

With reference to FIGS. 4*a* to 4*f* it will now be described how the flow characteristics of a liquid F flowing into the cavity 10 are controlled by the recesses 13:

Thus, the inflowing liquid F first of all flows onto the first of the cavities 13 in a direction of flow S (FIG. 4*a*).

The liquid F is initially stopped and deflected at the first region 14 or at the boundary edge 22 (FIG. 4*b*).

The liquid F continues on to the first region 14 of the second recess 13 and again to the second region 15 of the first recess 13, as a result of which the liquid F fills the first recess 13 through the second region 15 (cf. the dashed arrow in FIG. 4*c*).

The liquid F is then stopped and deflected again at the first region 14 of the second recess 13 and the cavity 10 is filled completely, initially leaving the second recess 13 free (cf. FIG. 4*d*).

As soon as the liquid F reaches the second region 15 of the second recess 13, the second recess 13 is also filled through the second region 15 (ramp-like transition (R)). The liquid front of the liquid F then extends to the first region 14 of the last recess 13 (FIG. 4*e*).

At the first region 14 the liquid F is again initially stopped and deflected until it then reaches the second region 15 of the last recess 13 and, proceeding from that point, fills the latter.

The filling process extends as far as the capillary stop 24 in the region of the outlet opening 12 and proceeds with substantially no air inclusions (air bubbles) (cf. FIG. 4*f*).

As a result of the alternating arrangement of the recesses 13, the liquid F is directed in a substantially meandering configuration through the cavity 10.

FIGS. 1 to 4 show that the second region 15 does not extend over the entire length L of a recess 13 but makes up only part of this length. Moreover, the region 15 also occupies a width which is significantly less than the width B of the recess 13 as a whole. In particular, the width of the region 15 is preferably less than half the width B of the recess 13. As a result it is possible to make good use of the volume of the recess 13 with an adequate fill function of the region 15.

In a departure from the embodiment shown, in which the regions 15 are positioned on the longitudinal sides of the recesses 13 remote from the incoming liquid F, it is also possible, however, to provide such regions at least partly on the transverse sides of the recesses 13 (cf. the dashed lines 15' in FIG. 1). It is also possible to provide a plurality of such regions on a recess (cf. also reference numerals 43 in FIG. 6).

FIG. 5 now shows a second embodiment 3 of a microfluidic structure of a microfluidic component 4. In contrast to the microfluidic structure 1 according to FIGS. 1 to 4, the microfluidic structure 3 comprises a cavity 30 with slightly differently configured recesses 31. Each recess 31 is in turn provided with a first region 32 in the form of a stop edge (capillary stop) which faces the direction of flow S of an incoming liquid. On the longitudinal side of the recess 31 remote away from the incoming liquid there is in turn a second region 33 in the form of a ramp, the region 33 extending over an entire length L of the recess 31. The width of the region 33 in turn amounts to at most only half a width B of the recess 31. In this embodiment as well, a meandering flow is created for an incoming liquid by the alternating arrangement of the recesses 31.

With reference to FIG. 6, a third embodiment of the invention will now be described. A microfluidic structure 5 on a microfluidic component 6 is shown which (in contrast to the preceding embodiments) has a cavity 40 which is curved, viewed in the direction of inflow S of a liquid.

Seven recesses 41 are provided in the cavity 40, each recess 41 having a longitudinal extent L and being of a curved configuration over this length L. Moreover it is apparent that each recess 41 is in turn provided with a first region 42 in the form of a stop edge (comparable with region 14 of the first embodiment) and, at the longitudinal side remote from the incoming liquid, comprises two regions 43 in the form of a ramp (comparable with the region 15 in the first embodiment).

An incoming liquid is initially stopped and deflected at the regions 42 and after reaching the regions 43 the process of filling each recess 41 begins until the liquid runs right on to the next recess 41. Thus the cavity 40 is filled step by step without any appreciable air inclusions.

Finally, with reference to FIGS. 7 and 8, the prior art will be briefly discussed.

These Figures show a microfluidic structure 7 of a microfluidic component 8 in which, in contrast to the embodiments according to the invention, a cavity 50 comprises not recesses but bars 51. The bars 51 are arranged alternately, starting from longitudinal sides of the cavity 50, and are intended to allow a meandering flow of an incoming liquid (not shown) and hence filling of the cavity 50 substantially free from air bubbles. The bars 51 start from a base 53 of the cavity 50 and extend to a cover 52 which closes off the cavity 50 at the top.

It is readily apparent that the inserted bars 51 significantly restrict the useful volume of the cavity 50.

LIST OF REFERENCE NUMERALS

1 Microfluidic structure
2 Microfluidic component
3 Microfluidic structure
4 Microfluidic component
5 Microfluidic structure
6 Microfluidic component
7 Microfluidic structure
8 Microfluidic component
10 Cavity
11 Inlet opening
12 Outlet opening
13 Recess
14 First region of the recess (stop edge)
15 Second region of the recess (ramp)
15' Second region of alternative design
15" Second region of alternative design (concave rounded portion)
15'" Second region of alternative design (convex rounded portion)
16 Fill channel
17 Venting channel
18 Further microchannel
19 Base of cavity
20 Base of recess
21 Cover
22 Boundary edge of recess
23 Boundary edge of recess
24 Capillary stop
30 Cavity
31 Recess
32 First region of recess (stop edge)
33 Second region of recess (ramp)
40 Cavity
41 Recess
42 First region of recess (stop edge)
43 Second region of recess (ramp)
50 Cavity
51 Bar
52 Cover
53 Base of recess
α Angle
β Angle
B Width of recess F Liquid
L Longitudinal extent of recess
R Ramp-like transition region
S Direction of flow of an incoming liquid

The invention claimed is:

1. A microfluidic structure (1, 3, 5), comprising:

at least one cavity (10, 30, 40) having: (i) a base wall (19); (ii) at least one inlet opening (11) at a first end of the at least one cavity, (iii) at least one outlet opening (12) at a second end of the at least one cavity, opposite to the first end and defining a longitudinal direction therebetween through the at least one cavity; (iv) first and second side walls disposed opposite to one another and laterally with respect to the longitudinal direction extending between the first and second ends, where the cavity (10, 30, 40) is adapted to be filled with a liquid (F) or have such a liquid flow through the cavity (10, 30, 40);

a cover extending over the at least one cavity opposite to the base wall, thereby defining a volume through which the liquid (F) flows; and at least one element (13, 31, 41) extending transversely with respect to the longitudinal direction from a proximal end at the first side wall to a distal end terminating short of the second sidewall, wherein the at least one element (13, 31, 41) having a recess (13, 31, 41) starting at the base wall (19) of the cavity (10, 30, 40) and forming a concavity in a direction away from the cover, said recess (13, 31, 41) having:

(i) at least one first region (14, 32, 42) extending along a first side of the recess and directed toward the at least one inlet opening (11) such that when the liquid (F) flows from the at least one inlet opening (11) in the longitudinal direction, the liquid (F) is configured to be at least temporarily stopped and/or at least partly deflected from entering the recess by at least one first region (14, 32, 42) and is blocked by the first side wall such that the liquid flows transversely to the longitudinal direction, along the recess, and towards and around the distal end of the recess, and (ii) at least one second region (15, 15', 5'', 15''', 33, 43) extending along a second side of the recess, opposite to the first side of the recess and directed toward the at least one outlet opening (12), such that when the liquid (F) flows around the distal end of the recess, the liquid (F) encounters the at least one second region and preferably flows into the recess (13, 31, 41).

2. The microfluidic structure (1, 3, 5) according to claim 1, wherein the second region (15, 33, 43) is formed by a ramp-like transition (R) which, starting from a base level (19) of the cavity (10), extends to a base level (20) of the recess (13).

3. The microfluidic structure (1, 3, 5) according to claim 1, wherein the ramp-like transition (R), starting from a boundary edge (23) of the recess (13), forms an angle α of approximately 10° to 60°, particularly preferably about 45°, with the base plane (19) of the cavity (10).

4. The microfluidic structure (1, 3, 5) according to claim 1, wherein the first region (14, 32, 42) is formed by a boundary edge (22) of the recess (13), at which the convergent walls forming the boundary edge (22) form an angle β which is less than 120°, particularly preferably about 90°.

5. The microfluidic structure (1, 3, 5) according to claim 1, wherein the at least one recess (13, 31, 41) is of elongate formation, the at least one first region (14, 32, 42) facing an incoming liquid (F) and the at least one second region (15, 33, 43) being remote from an incoming liquid (F).

6. The microfluidic structure (1, 3) according to claim 1, wherein a plurality of recesses (13, 31, 41) are provided which are arranged alternately, starting from side walls of the cavity (10, 30, 40).

7. The microfluidic structure (1, 5) according to claim 1, wherein the at least one first region (14, 32, 42) extends over substantially the entire length (L) of a longitudinal side of the at least one recess (13, 31, 41) and the at least one second region (15, 33, 43) extends over only part of the length (L) of another longitudinal side.

8. A microfluidic platform (2, 4, 6) having at least one microfluidic structure (1, 3, 5) comprising:

at least one cavity (10, 30, 40) having: (i) a base wall (19); (ii) at least one inlet opening (11) at a first end of the at least one cavity, (iii) at least one outlet opening (12) at a second end of the at least one cavity, opposite to the first end and defining a longitudinal direction therebetween through the at least one cavity; (iv) first and second side walls disposed opposite to one another and laterally with respect to the longitudinal direction extending between the first and second ends, where the cavity (10, 30, 40) is adapted to be filled with a liquid (F) or have such a liquid flow through the cavity (10, 30, 40);

a cover extending over the at least one cavity opposite to the base wall, thereby defining a volume through which the liquid (F) flows; and at least one element (13, 31, 41) extending transversely with respect to the longitudinal direction from a proximal end at the first side wall to a distal end terminating short of the second sidewall, wherein the at least one element (13, 31, 41) having a recess (13, 31, 41) starting at the base wall (19) of the cavity (10, 30, 40) and forming a concavity in a direction away from the cover, said recess (13, 31, 41) having:

(i) at least one first region (14, 32, 42) extending along a first side of the recess and directed toward the at least one inlet opening (11) such that when the liquid (F) flows from the at least one inlet opening (11) in the longitudinal direction, the liquid (F) is configured to be at least temporarily stopped and/or at least partly deflected from entering the recess by at least one first region (14, 32, 42) and is blocked by the first side wall such that the liquid flows transversely to the longitudinal direction, along the recess, and towards and around the distal end of the recess, and (ii) at least one second region (15, 15', 5'', 15''', 33, 43) extending along a second side of the recess, opposite to the first side of the recess and directed toward the at least one outlet opening (12), such that when the liquid (F) flows around the distal end of the recess, the liquid (F) encounters the at least one second region and preferably flows into the recess (13, 31, 41).

* * * * *